United States Patent
Church et al.

(10) Patent No.: US 10,202,132 B2
(45) Date of Patent: Feb. 12, 2019

(54) MONITORING DEVICE FOR MONITORING A RAILWAY TRACK, ASSOCIATED METHOD AND MONITORING SYSTEM FOR MONITORING A RAILWAY TRACK

(71) Applicant: ALSTOM TRANSPORT TECHNOLOGIES, Saint-Ouen (FR)

(72) Inventors: Benjamin Church, Blue Springs, MO (US); Darren Melton, Grain Valley, MO (US)

(73) Assignee: ALSTOM TRANSPORT TECHNOLOGIES, Saint-Ouen (FR)

( * ) Notice: Subject to any disclaimer, the term of this patent is extended or adjusted under 35 U.S.C. 154(b) by 0 days.

(21) Appl. No.: 15/462,125

(22) Filed: Mar. 17, 2017

(65) Prior Publication Data

US 2018/0265106 A1    Sep. 20, 2018

(51) Int. Cl.
| | |
|---|---|
| *B61L 1/18* | (2006.01) |
| *B61L 23/04* | (2006.01) |
| *G01N 27/04* | (2006.01) |
| *B61L 25/02* | (2006.01) |

(52) U.S. Cl.
CPC ............. *B61L 23/044* (2013.01); *B61L 1/188* (2013.01); *B61L 25/025* (2013.01); *G01N 27/041* (2013.01)

(58) Field of Classification Search
CPC ................................ B61L 23/044; B61L 1/18
USPC .............. 324/500, 512, 527, 532, 535, 76.11, 324/76.12, 76.22, 76.66, 600, 629, 637, 324/639, 217, 218
See application file for complete search history.

(56) References Cited

U.S. PATENT DOCUMENTS

| | | | | |
|---|---|---|---|---|
| 4,389,033 A | * | 6/1983 | Hardman | B61L 23/044 246/28 F |
| 4,498,650 A | * | 2/1985 | Smith | B61L 1/188 246/122 R |
| 4,886,226 A | * | 12/1989 | Frielinghaus | B61L 23/041 246/121 |
| 9,771,090 B2 | * | 9/2017 | Warta | B61L 23/042 |
| 2002/0033049 A1 | * | 3/2002 | Amini | B61K 9/10 73/636 |
| 2007/0132463 A1 | * | 6/2007 | Anderson | B61L 1/181 324/713 |
| 2008/0117043 A1 | * | 5/2008 | Van Den Abeele | B61B 1/02 340/540 |
| 2011/0147535 A1 | * | 6/2011 | Aisa | B61L 1/187 246/122 R |
| 2012/0138752 A1 | * | 6/2012 | Carlson | B61L 1/164 246/126 |

(Continued)

*Primary Examiner* — Patrick Assouad
*Assistant Examiner* — Demetrius R Pretlow
(74) *Attorney, Agent, or Firm* — Troutman Sanders LLP

(57) ABSTRACT

A monitoring device monitoring a railway track, including a track interface connecting the monitoring device to the railway track. Also included is a detector detecting a first track pulse having a first duration emitted on the railway track and received through the track interface. The detector can detect a start and end time of the first track pulse. A charger is connected to the detector and has an energy storage element. Further, there is an emitter emitting a second track pulse on the railway track through the track interface by using energy stored in the energy storage element and the detector can send a transmit control signal to the emitter.

11 Claims, 2 Drawing Sheets

(56) References Cited

U.S. PATENT DOCUMENTS

2014/0238139 A1* 8/2014 Loveday .............. G01N 29/043
73/632
2017/0203776 A1* 7/2017 Fuchs ................. B61L 27/0077

* cited by examiner

MONITORING DEVICE FOR MONITORING A RAILWAY TRACK, ASSOCIATED METHOD AND MONITORING SYSTEM FOR MONITORING A RAILWAY TRACK

FIELD OF INVENTION

The present invention relates to a monitoring device configured for monitoring a railway track, the monitoring device comprising a track interface, a detector, a charging module and an emitter. The present invention relates more particularly to track occupancy detection and broken rail detection.

BACKGROUND

In general, the present invention relates to the domain of automatic train control architectures and other train control architectures for trains traveling on a railroad network.

In such train control architectures, the railroad network is made up of railroad track sections. The detection of rail breakage and the detection of trains present in the corresponding track section are key pieces of information for railroad safety. To provide such information, besides other information, railway tracks are equipped with track controllers.

Such track controllers are known in the art. They are integrated in a train control system and they are configured to emit and receive signals or pulses carried by the rail. For this end, each track controller is electrically connected to the rails.

For example, at each boundary of a track section, a track controller is installed. The track controller is configured to emit pulses into the rail. In particular, pulses are emitted at first end of a track section by the corresponding track controller, and received by another track controller which is installed at the second end of a track section. The width and spacing of the pulses received provide information that may be used to control railroad signal aspects at the location. The transmission is only successful if the rail is in good order, i.e. not broken. By receiving a pulse at the second end, it is thus determined that the rail in the corresponding track section is not broken and no train is occupying the track section. Besides this, track controllers provide for example detection of trains in the corresponding track section. Furthermore, track controllers provide for example approach lighting control. In this case, the controller will only light a railroad signal when an approaching train enters the adjacent track section.

However, providing a track controller of the type described above to every end of a track section relates to several drawbacks.

For example, such track controllers require power to operate. Complex power cable systems must be installed for power supply of each track controller. Power cables, for example made out of copper, may be stolen and in consequence, the track controller may be out of operation. Additionally, in the installation phase, the laying of the power cables for each track controller requires an additional installation step. Besides required cables, equipment houses and charging systems for powering the track controller must be installed and maintained.

Furthermore, providing every end of a track section with a track controller constitutes a complex system as such track controllers must be maintained at regular intervals to ensure their correct operation. Additionally, track controllers may be subject to vandalism which may cause the track controllers to be out of service.

SUMMARY

The present invention aims to resolve the aforementioned problems, notably at locations adjacent to non-signaled territory where only broken rail detection and track circuit occupancy detection is required.

To that end, the invention relates to a monitoring device configured for monitoring a railway track, said monitoring device comprising:
- a track interface configured for connecting the monitoring device to the railway track,
- a detector, configured for detecting a first track pulse having a first duration emitted on the railway track and received through the track interface, the detector being further configured for detecting a start time of the first track pulse, which corresponds to the detection of a start of a receiving period and for detecting an end time of the first track pulse, which corresponds to the detection of a start of a transmission period,
- a charging module connected to said detector, said charging module comprising an energy storage element, the charging module being configured to store energy received from the first track pulse in the energy storage element,
- an emitter, configured for emitting a second track pulse on the railway track through the track interface by using the energy stored in the energy storage element, the second track pulse having a second duration less than the first duration of the first track pulse,
- the detector being configured for sending a transmit control signal to the emitter for controlling the emission of the second track pulse by the emitter when the detector detects the end time of the first track pulse.

The monitoring device according to the invention is thus configured to harvest energy from the track contained in the first track pulse. This is effectuated by the charging module when the first track pulse is detected. The harvested energy is stored and used for emission of the second track pulse into the track. This second track pulse is designated to be received by a track controller distinct from the monitoring device.

Thus, the monitoring device according to the invention does not require an external power supply. No cables for power supply of the monitoring device are necessary.

According to advantageous but not mandatory aspects of the invention, such a monitoring device may incorporate one or several of the following features, taken in any technically admissible combination:
- the emitter is configured for monitoring the energy stored in the energy storage element, for comparing the energy stored to a predetermined energy threshold, and for emitting the second track pulse only if the energy stored is higher than said predetermined energy threshold;
- the emitter is configured for comparing the energy stored to a predetermined energy threshold which varies according to a length of a track section to which the monitoring device is connected;
- the charging module comprises a charging circuit, configured for collecting the current received from the first track pulse, for transforming said current into a transformed current having a current level required for storing the energy of the first track pulse in the energy storage element, and for charging the energy storage element with said transformed current;

the charging circuit is switchable between an active state, wherein the charging circuit is able to charge the energy storage element, and an inactive state, wherein the charging circuit disconnects electronically the energy storage element and the track interface;

the detector is configured for sending an activation signal to the charging circuit for switching the charging circuit from the inactive state to the active state when the detector detects the start time of the first track pulse, and for sending an inactivation signal to the charging circuit for switching the charging circuit from the active state to the inactive state when the detector detects the end time of the first track pulse;

the first track pulse is a code 6 pulse and the second track pulse is a code 1 pulse;

the emitter is configured for emitting a second track pulse only if no second track pulse was emitted in the precedent transmission period;

the emitter is configured for emitting a second track pulse only if no second track pulse was emitted in any of the N precedent transmission periods, where N is an integer greater than 1;

The invention further relates to a monitoring system for monitoring a railway track, comprising:

a monitoring device as previously described, a track controller, configured for emitting the first track pulse through the railway track, for receiving the second track pulse emitted by the monitoring device on the railway track, and for analyzing the second track pulse to determine a railway track feature.

The monitoring system according to the invention is thus configured to determine required railway track features such as for example train detection, rail breakage detection or approach lighting control by using a monitoring system comprising only one track controller per track section and a monitoring device according to the invention.

The invention further relates to a method for monitoring a railway track, said method comprising:

detecting a first track pulse having a first duration emitted on the railway track and received through a track interface, detecting a start time of the first track pulse, which corresponds to the detection of a start of a receiving period, storing energy received from the first track pulse in an energy storage element, detecting an end time of the first track pulse, which corresponds to the detection of a start of a transmission period sending a transmit control signal to an emitter for controlling the emission of a second track pulse by the emitter when the end time of the first track pulse is detected, and emitting the second track pulse on the railway track through the track interface by using the energy stored in the energy storage element, the second track pulse having a second duration less than the first duration of the first track pulse.

BRIEF DESCRIPTION OF THE DRAWINGS

The invention and other advantages thereof will become more clearly apparent in the light of the description which follows of an embodiment of a monitoring device according to the invention, only given as an example and made with reference to the appended drawings wherein.

DETAILED DESCRIPTION

Figure 1:
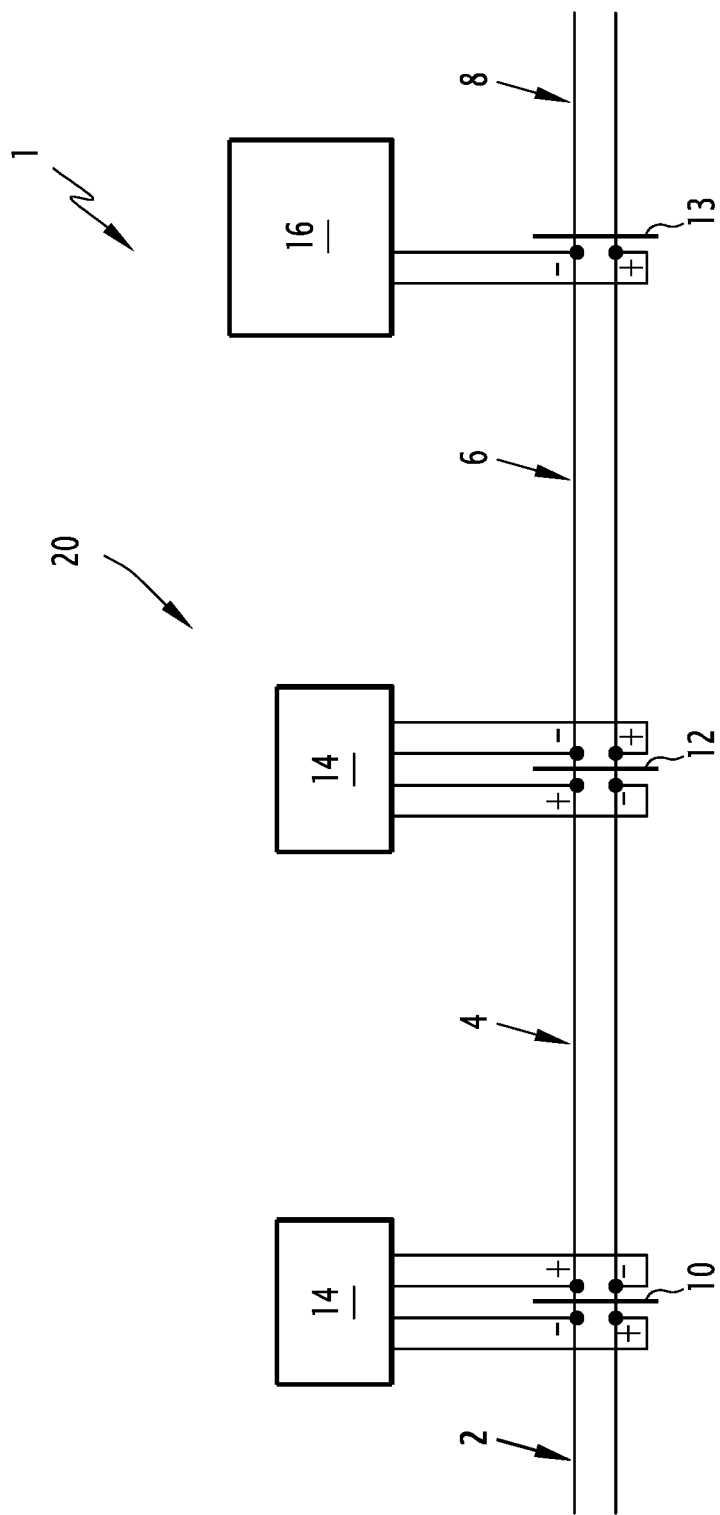
FIG. 1 is a diagram of a railway track provided with two track controllers and a monitoring device according to the invention.

With reference to FIG. 1, a railway track 1 containing several track sections 2, 4, 6, 8 is shown. The track sections 2, 4, 6, 8 are electrically separated by section boundaries 10, 12, 13. At the section boundaries 10, 12, a track controller 14 is installed respectively.

Each track controller 14 is connected to both rails on both sides of the corresponding section boundary 10, 12. Each track controller 14 is configured for emitting first track pulses through the railway track 1 of the corresponding section 2, 4, 6. A first rail of each track section 2, 4, 6 is supplied with pulses that contain positive charge + and a second rail is supplied with pulses that contain a negative charge −. The sign of the charge in the corresponding rail can differ from one track section 2, 4, 6 to another, as the sections 2, 4, 6 are electrically separated.

Each track controller 14 is further configured for receiving second track pulses emitted on the railway track, and for analyzing the second track pulses to determine a railway track feature. For example, each track controller 14 is configured to be connected to a railroad signal controller which is configured to light one or more railroad signals based upon the received track code information obtained from the track controller. Thus, the railroad signal aspect conveyed to the train engineer provides necessary information required to safely operate a railway vehicle.

For example, in track section 6, only at section boundary 12 a track controller 14 is installed. Without installation of a second track controller 14 at the second boundary 13, the track section 6 would be not controlled and track features such as rail breakages would be not determined. To provide such determination capability of track features, on the other end of track section 6, at section boundary 13, a monitoring device 16 according to the invention is installed.

The monitoring device 16 is configured for detecting a first track pulse and for emitting the second track pulse on the railway track 1 by using energy stored inside the monitoring device 16. The monitoring device 16 is not connected to a power cable and does not require any cable connection to other devices. Thus, the monitoring device 16 is connected solely to railway track 1.

The energy required for emitting the second track pulse is harvested from the railway track 1 by the monitoring device 16 and stored inside the monitoring device 16. In particular, the required energy is harvested from the first pulse that is transmitted on the railway track 1, especially from the first pulse transmitted by the track controller 14.

The first track pulse is longer than the second track pulse. This allows the monitoring device 16 to harvest enough energy for emitting the second track pulse.

The first track pulse has preferably a duration between 500 and 700 ms, for example 600 ms. The first track pulse is for example a code 6 pulse according to the standard freight ElectroCode.

The second track pulse has preferably a duration between 90 and 120 ms, for example 112 ms. The second track pulse is for example a code 1 pulse according to the standard freight ElectroCode.

For example, the standard ElectroCode cycle has a duration of 2.8 s and is split evenly with 1.4 s for receiving track pulses (receiving period) and 1.4 s for transmitting track pulses (transmission period) into the railway track 1. For example, the first track pulse sent from track controller 14 is transmitted during its transmit period and is received by the monitoring device 16. The monitoring device 16 is configured to transmit back the second track pulse during its transmit period which is received by the track controller 14 during the track controller's receive period.

The track controller 14 and the monitoring device 16 constitute together a monitoring system 20 which is configured to provide information for the determination of a track feature.

Figure 2:
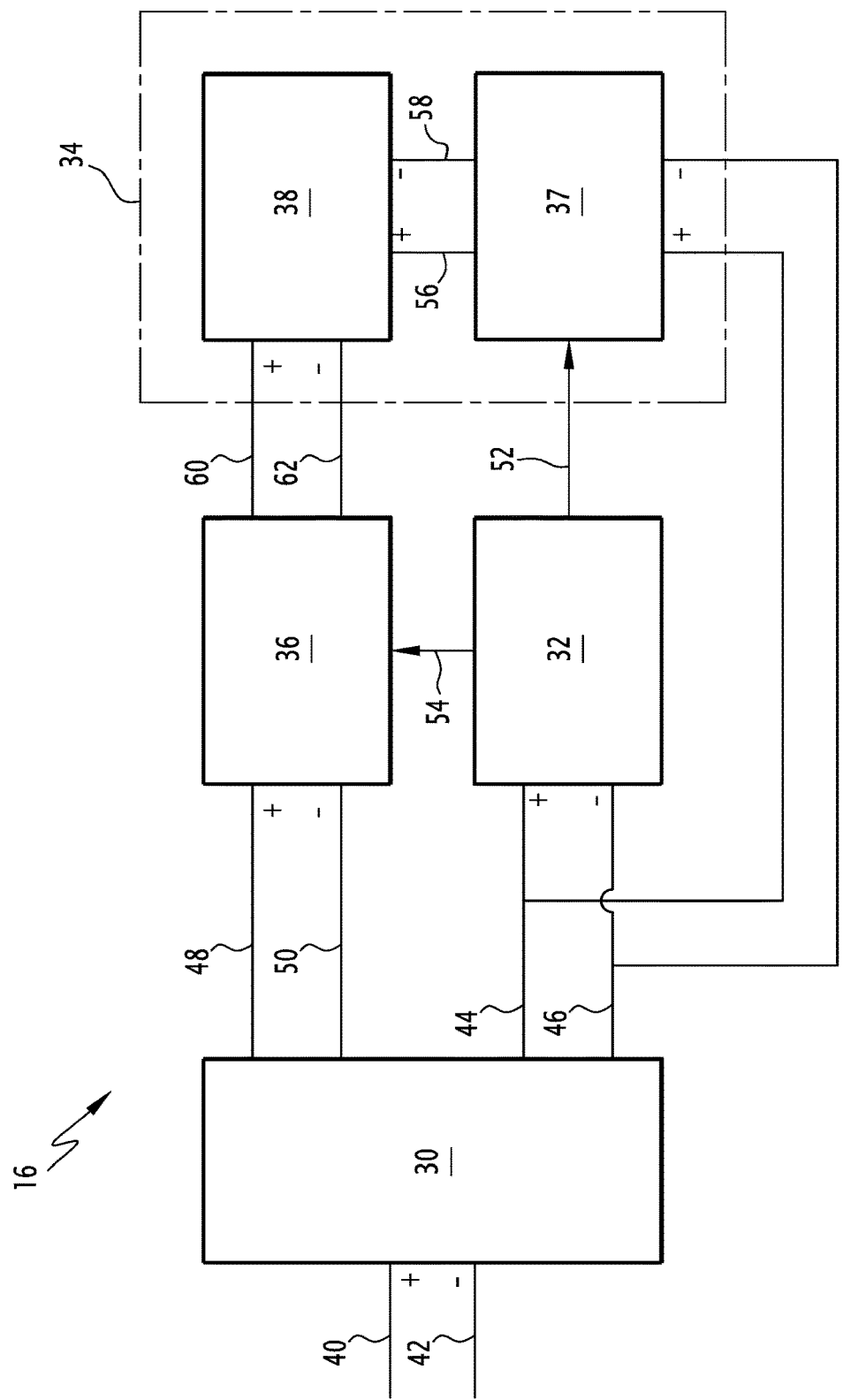
FIG. 2 is a functional diagram of the monitoring device according to the invention.

With reference to FIG. 2, the architecture of the monitoring device will be described further in detail.

The monitoring device 16 includes a track interface 30, which is electrically connected to a detector 32, a charging module 34 and an emitter 36. The charging module 34 includes a charging circuit 37 and an energy storage element 38.

Preferably, the track interface 30 is directly connected to each of the detector 32, the charging module 34 and the emitter 36.

The track interface 30 is configured to be connected to both rails of the railway track 1. Electrical connections between the rail and the track interface 30 are made out of cables, for example copper cables. The cables are for example welded or fixed by mechanical fixations to the each rail and represent inputs into the track interface 30.

Depending on the charge of the corresponding rail, a first input 40 contains a positive charge and a second input 42 contains a negative charge. The track interface 30 is configured for distributing these inputs to the detector 32 and to the charging module 34 by an output 44, which contains a positive charge, and by an output 46, which contains negative charge.

Furthermore, the track interface 30 is configured to be connected to the emitter 36 by a connection 48 which contains a positive charge and by a connection 50 which contains a negative charge.

The detector 32 is configured for detecting the start of the receiving period which corresponds to a start time of the first track pulse. Further, the detector 32 is configured for detecting the first track pulse emitted on the railway track 1 and received through the track interface 30. The pulse is for example emitted by the corresponding track controller 14 installed in the track section 6.

The detector 32 is further configured for sending an activation signal to the charging circuit 37 in the charging module 34 via an output 52 for switching the charging circuit 37 from an inactive state to an active state, when the detector 32 detects the start of a receiving period corresponding to receiving a first track pulse. When no first track pulse energy is detected on the track interface 30 during the receiving period, the detector 32 is configured to transition back to the inactive state and to send an inactivation signal to the charging circuit for the remainder of the receiving period. This prevents the energy storage element for being drained.

The detector 32 is further configured for detecting the start of the transmission period corresponding to an end time of the receiving period. During the transmission period, no pulse is received from the track controller 14 in the railway track 1.

The detector 32 is further configured for sending an inactivation signal to the charging circuit 37 in the charging module 34 via the output 52 for switching the charging circuit from the active state to the inactive state at the start of the transmission period.

The detector 32 is further configured for sending a transmit control signal to the emitter 36 via an output 54 for controlling the emission of the second track pulse by the emitter 36 when the detector 32 detects the start of the transmission period.

The detector 32 contains therefore a state machine, not represented, that is configured to send the activation signal, the inactivation signal and the transmit control signal on the conditions described above.

The detector 32 is for example a state machine that may be implemented in a Field-Programmable Gate Array or any other circuitry.

The charging module 34 is configured to store energy received from the first track pulse in the energy storage element 38. For example, the first track pulse contains such energy to store in the energy storage element 38.

The charging circuit 37 of the charging module 34 is in particular configured for collecting the current received from the first track pulse, for transforming the current into a level required for storing the energy of the first track pulse in the energy storage element 38. The charging circuit 37 is configured for charging the energy storage element 38 with the transformed current.

The charging circuit 37 is switchable between the active state, wherein the charging circuit 37 is able to charge the energy storage element 38, and the inactive state, wherein the charging circuit 37 is shut down to prevent the energy storage element 38 from draining energy through the charging circuit 37 to outputs 44, 46 then through the track interface 30.

The energy storage element 38 is configured to store energy which is obtained from the charging circuit 37 in the required current level as described above, via connections 56 and 58. The energy storage element 38 is for example a supercapacitor, also called electric double-layer capacitors, a capacitor bank or a battery such as a lithium-ion battery or any other type of battery.

The emitter 36 is configured for emitting the second track pulse on the railway track 1 through the track interface 30 by using the energy stored in the energy storage element 38.

The emitter 36 is further configured for monitoring the energy stored in the energy storage element 38. It is configured for comparing the stored energy to a predetermined energy threshold. Based on this comparison, it is further configured for emitting the second track pulse only if the stored energy is higher than said predetermined energy threshold.

The emitter 36 is for example integrated in a Field-Programmable Gate Array, contains a digital signal processor or any other circuitry.

The length of the track section, track ballast conditions, and application requirements will determine the emitter parameters such as the minimum required stored energy and transmit rate required for the second track pulse. These parameters may be embodied in several hard-wired configurations or as user-selectable configurations of the emitter 36.

The emitter 36 requires more energy to emit the second track pulse into the long track section 6 than in a shorter track section 6. Therefore, the energy threshold is preferably higher when the corresponding track section 6 is longer.

In order not to emit a pulse unnecessarily often, the emitter 36 is preferably configured for emitting the second track pulse only if no second track pulse was emitted in the precedent transmission period. There is no need to send the pulse every transmission period as with such functioning an effective transmission period is, as described above, for example shorter than 4.2 s.

Alternatively, the emitter 36 is configured for emitting the second track pulse only if no second track pulse was emitted in any of the n precedent transmission periods, n being an integer. For example, on railway tracks 1 that are less frequented, information about the track feature may be required one time per minute only. Thus, in order to conserve energy in the energy storage element 38, the emitter 36 is preferably configured to emit the second pulse at a minimum required frequency only.

In the following, an example of the operation of the monitoring system will be described.

With reference to FIG. 1, the track section 6 contains one track controller 14 and one monitoring device 16. The track controller 14 emits during its receiving period the first pulse in the track 1.

With reference to FIG. 2, the detector 32 detects the start of the receiving period which corresponds to a start time of the first track pulse. In particular, the detector 32 detects the first track pulse emitted on the railway track 1 and received through the track interface 30. The first track pulse is for example emitted by the corresponding track controller 14 installed in track section 6. By detection of the first track pulse, the detector 32 sends an activation signal to the charging circuit 37 in the charging module 34 via the output 52 for switching the charging circuit 37 from an inactive state to an active state. In consequence, the charging circuit 37 starts harvesting energy from the first track pulse. In particular, the charging circuit 37 collects current received from the first track pulse and transforms the current into a level required for storing the energy of the first track pulse in the energy storage element 38. The charging circuit 37 charges thus the energy storage element 38 with the converted current.

When the detector 32 detects the end of the first track pulse, it sends an inactivation signal to the charging circuit 37 in the charging module 34 via the output 52 for switching the charging circuit 37 from the active state to the inactive state. The start of the transmission period corresponds to the end of the receiving period.

At the start of the transmission period, the detector 32 sends transmit control signal to the emitter 36 via the output 54 for controlling the emission of the second track pulse by the emitter 36.

The emitter 36 monitors the energy stored in the energy storage element 38. It compares the energy stored in the energy storage element 38 to the predetermined energy threshold. If the energy stored is higher than the predetermined energy threshold and the emitter 36 received the transmit control signal of the detector 32, the emitter 36 emits the second track pulse on the railway track 1 through the track interface 30 by using the energy stored in the energy storage element 38.

The second track pulse is transmitted by the monitoring device 16 during its transmit period.

The second track pulse is received by the track controller 14 of the corresponding track section 6 during the track controller's receive period.

For example, it is desired to detect a rail breakage in track section 6. The track controller 14 determines this track feature by analyzing the second track pulse emitted by the monitoring device 16. In particular, the track controller 14 detects that a rail is actually broken by analyzing the time of no reception of the second track pulse, as the transmission of such pulse may be interrupted in this case.

As explained above, in order not to emit a pulse unnecessarily often, the emitter 36 preferably emits the second track pulse only if no second track pulse was emitted in the precedent transmission period, or only if no second track pulse was emitted in any of the n precedent transmission periods, n being an integer for example in the interval from 1 to 20. For example, on railway tracks 1 that are less frequented, information about the track feature may be required one time per minute only. Thus, in order to conserve energy in the energy storage element 38, the emitter 36 preferably emits the second pulse at a minimum required frequency only.

In such case, the track controller 14 detects that a rail is actually broken when no second track pulse is received during a predetermined period.

At the start of the subsequent receiving period, the detector 32 detects the first pulse again and sends an activation pulse to the charging circuit 37 which starts harvesting energy from the first pulse again. The above described operation steps are repeated.

Besides, when no first track pulse energy is detected on the track interface 30 during a given receiving period, the detector 32 transitions back to the inactive state and send an inactivation signal to the charging circuit for the remainder of the receiving period.

The monitoring device 16 according to the invention is, for example, protected by an environmentally hardened box that can be buried in the ballast. Maintenance costs are very low as the device does not require any power supply. Additionally, the risk of vandalism is reduced as the box is for example hidden in the track ballast.

The invention claimed is:

1. A monitoring device configured for monitoring a railway track, said monitoring device comprising:
    a track interface configured for connecting the monitoring device to the railway track,
    a detector, configured for detecting a first track pulse having a first duration emitted on the railway track and received through the track interface, the detector being further configured for detecting a start time of the first track pulse, which corresponds to the detection of a start of a receiving period and for detecting an end time of the first track pulse, which corresponds to the detection of a start of a transmission period,
    a charging module connected to said detector, said charging module comprising an energy storage element, the charging module being configured to store energy received from the first track pulse in the energy storage element,
    an emitter, configured for emitting a second track pulse on the railway track through the track interface by using the energy stored in the energy storage element, the second track pulse having a second duration less than the first duration of the first track pulse,
    the detector being configured for sending a transmit control signal to the emitter for controlling the emission of the second track pulse by the emitter when the detector detects the end time of the first track pulse.

2. A monitoring device according to claim 1, wherein the emitter is configured for monitoring the energy stored in the energy storage element, for comparing the energy stored to a predetermined energy threshold, and for emitting the second track pulse only if the energy stored is higher than said predetermined energy threshold.

3. A monitoring device according to claim 2, wherein the emitter is configured for comparing the energy stored to a predetermined energy threshold which varies according to a length of a track section to which the monitoring device is connected.

4. A monitoring device according to claim 1, wherein the charging module comprises a charging circuit, configured for collecting the current received from the first track pulse, for transforming said current into a transformed current having a current level required for storing the energy of the first track pulse in the energy storage element, and for charging the energy storage element with said transformed current.

5. A monitoring device according to claim 4, wherein the charging circuit is switchable between an active state, wherein the charging circuit is able to charge the energy storage element, and an inactive state, wherein the charging circuit disconnects electronically the energy storage element and the track interface.

6. A monitoring device according to claim 5, wherein the detector is configured for sending an activation signal to the charging circuit for switching the charging circuit from the inactive state to the active state when the detector detects the start time of the first track pulse, and for sending an inactivation signal to the charging circuit for switching the charging circuit from the active state to the inactive state when the detector detects the end time of the first track pulse.

7. A monitoring device according to claim 1, wherein the first track pulse is a code 6 pulse and the second track pulse is a code 1 pulse.

8. A monitoring device according to claim 1, wherein the emitter is configured for emitting a second track pulse only if no second track pulse was emitted in the precedent transmission period.

9. A monitoring device according to claim 1, wherein the emitter is configured for emitting a second track pulse only if no second track pulse was emitted in any of the N precedent transmission periods, where N is an integer greater than 1.

10. A monitoring system for monitoring a railway track, comprising:
a monitoring device according to claim 1,
a track controller, configured for emitting the first track pulse through the railway track, for receiving the second track pulse emitted by the monitoring device on the railway track, and for analyzing the second track pulse to determine a railway track feature.

11. Method for monitoring a railway track, said method comprising:
detecting a first track pulse having a first duration emitted on the railway track and received through a track interface,
detecting a start time of the first track pulse, which corresponds to the detection of a start of a receiving period,
storing energy received from the first track pulse in an energy storage element,
detecting an end time of the first track pulse, which corresponds to the detection of a start of a transmission period
sending a transmit control signal to an emitter for controlling the emission of a second track pulse by the emitter when the end time of the first track pulse is detected, and
emitting the second track pulse on the railway track through the track interface by using the energy stored in the energy storage element, the second track pulse having a second duration less than the first duration of the first track pulse.

* * * * *